United States Patent
Andersen et al.

(10) Patent No.: US 9,240,825 B2
(45) Date of Patent: Jan. 19, 2016

(54) MONITORING DEVICE AND A METHOD FOR WIRELESS DATA AND POWER TRANSMISSION IN A MONITORING DEVICE

(75) Inventors: Henning Hougaard Andersen, Lynge (DK); Soren Kilsgaard, Lynge (DK)

(73) Assignee: Widex A/S, Lynge (DK)

( * ) Notice: Subject to any disclaimer, the term of this patent is extended or adjusted under 35 U.S.C. 154(b) by 539 days.

(21) Appl. No.: 13/614,094

(22) Filed: Sep. 13, 2012

(65) Prior Publication Data
US 2013/0009609 A1    Jan. 10, 2013

Related U.S. Application Data

(63) Continuation-in-part of application No. PCT/EP2010/054534, filed on Apr. 6, 2010.

(51) Int. Cl.
| | | |
|---|---|---|
| *H02J 7/00* | (2006.01) | |
| *H04B 5/00* | (2006.01) | |
| *A61B 5/00* | (2006.01) | |
| *H02J 5/00* | (2006.01) | |
| *A61B 5/0476* | (2006.01) | |

(52) U.S. Cl.
CPC ............ *H04B 5/0031* (2013.01); *A61B 5/0002* (2013.01); *H02J 5/005* (2013.01); *H04B 5/0037* (2013.01); *H04B 5/0081* (2013.01); *A61B 5/0476* (2013.01); *A61B 2560/0219* (2013.01)

(58) Field of Classification Search
CPC ....................................................... H02J 5/005
USPC ................. 716/116–117, 133–136, 166–167; 320/108, 116–117, 133–136, 166–167
See application file for complete search history.

(56) References Cited

U.S. PATENT DOCUMENTS

| | | | |
|---|---|---|---|
| 5,260,701 A | 11/1993 | Guern et al. | |
| 6,167,094 A | 12/2000 | Reiner | |
| 6,301,138 B1 | 10/2001 | Amtmann | |
| 6,667,914 B2 | 12/2003 | Gomex | |
| 2001/0054881 A1* | 12/2001 | Watanabe | ..................... 320/166 |
| 2005/0163063 A1 | 7/2005 | Kuchler et al. | |

FOREIGN PATENT DOCUMENTS

| | | |
|---|---|---|
| CN | 101002504 A | 7/2007 |
| CN | 101425704 A | 5/2009 |

(Continued)

OTHER PUBLICATIONS

International Search Report with Wrtitten Opinion for PCT/EP2010/054534 dated Nov. 29, 2010.

(Continued)

*Primary Examiner* — Paul Dinh
(74) *Attorney, Agent, or Firm* — Sughrue Mion, PLLC

(57) ABSTRACT

In a monitoring device including a reader and a data carrier, the data carrier includes a receiver coil (201), a resonator capacitor (202), rectifier means (203), a modulation capacitor (206), an energy storage capacitor (204), three modulation switches (209, 210, 211) and data processing means. The modulation capacitor (206), the energy storage capacitor (204), the data processing means and the three modulation switches (209, 210, 211) are arranged such that, in a first configuration, the modulation capacitor (206) and the energy storage capacitor (204) are coupled in parallel and, in a second configuration, the modulation capacitor (206) and the energy storage capacitor (204) are coupled in series. The invention further provides a method of operating a data carrier in such a monitoring device.

6 Claims, 3 Drawing Sheets

(56) References Cited

FOREIGN PATENT DOCUMENTS

| | | |
|---|---|---|
| DE | 4444984 C1 | 12/1995 |
| WO | 0223471 A1 | 3/2002 |

OTHER PUBLICATIONS

Office Action for counterpart Chinese Application No. 201080065877.9 dated Dec. 23, 2013, with English translation.

\* cited by examiner

MONITORING DEVICE AND A METHOD FOR WIRELESS DATA AND POWER TRANSMISSION IN A MONITORING DEVICE

RELATED APPLICATIONS

The present application is a continuation-in-part of application No. PCT/EP2010/054534, filed on Apr. 6, 2010, in Europe and published as WO2011124251 A1.

BACKGROUND OF THE INVENTION

1. Field of the Invention

The present invention relates to monitoring devices. The invention more specifically relates to monitoring devices comprising a reader and a data carrier, adapted for wireless data and power transmission. The invention also relates to a method for operating a monitoring device.

In the context of the present disclosure a monitoring device should be understood as a small device designed to be worn by a human user for continuous surveillance of a specific medical condition in the user. The monitoring device consists of a reader and a data carrier.

The reader is powered by an internal primary energy source, such as a battery. The data carrier does not have its own primary source of energy. Therefore the data carrier relies on a wireless inductive power transmission from the reader. A transmitter coil in the reader and a receiver coil in the data carrier together form a system of magnetically coupled inductors. The basic principle relies on generating an alternating current in the transmitter coil. The current in the transmitter coil generates a magnetic field which induces a current in the receiver coil. The current in the receiver coil is used to power the data carrier.

The data carrier has monitoring means, such as electrodes for measuring EEG signals in the human user of the monitoring device. The data collected by the monitoring means are preprocessed by data processing means and wirelessly transmitted to the reader for further processing. The reader receives data from the data carrier through load modulation of the data carrier. In a typical application the further processing in the reader includes determining if a specific medical condition has occurred in the user and alerting the user of this condition. Hereby the size and power consumption of the data carrier can be kept small because the battery and the main part of the signal processing is placed in the reader. This is advantageous in that it makes the data carrier feasible for implantation in the human user. It is especially advantageous to have the data carrier subcutaneously implanted with respect to measurement of EEG signals.

2. The Prior Art

U.S. Pat. No. 5,260,701 discloses a device for the bi-directional transmission of data between a master system and a slave system that uses a single transmission antenna and a single reception antenna, wherein the slave system comprises a switching circuit connected in series between a rectifier circuit and a power supply circuit to modulate the real part of the impedance of the slave system between a high value and a low value when the switching circuit is driven in its opened and closed position by a control signal representative of the data to be transmitted to the master system.

U.S. Pat. No. 6,301,138 discloses a data carrier with load modulation means and with improved power supply in the process of load modulation. Additional means secure that the supply voltage for the data processing means during load modulation can be kept at least at the level of the load modulation during the load modulation pauses. The disclosed additional means includes a voltage multiplier circuit and a charge pump.

It is a feature of the present invention to provide a monitoring device incorporating a reader and a data carrier with improved means for data transmission and energy efficiency, hereby providing a monitoring device with a reduced power consumption.

It is another feature of the present invention to provide an improved method for operating a monitoring device.

SUMMARY OF THE INVENTION

The invention, in a first aspect, provides a monitoring device comprising a reader and a data carrier, adapted for wireless data transmission from the data carrier to the reader using load modulation and for powering the data carrier using a wireless inductive power transmission from the reader and to the data carrier, wherein the data carrier comprises a receiver coil, data processing means, rectifier means, switch means and at least two capacitors, wherein the data processing means, switch means and capacitors are connected such that, in a first configuration, the capacitors are coupled in parallel and, in a second configuration, the capacitors are coupled in series, whereby load modulation of the data carrier is achieved by switching between said first and second configuration, and said capacitors are further arranged for storing energy received from the wireless inductive power transmission and for powering the data processing means.

The invention, in a second aspect, provides A method of operating a data carrier in a monitoring device comprising the steps of providing in the data carrier a first capacitor, a second capacitor, switching means and data processing means, connecting the first capacitor, the second capacitor, the switching means and the data processing means, and operating the switching means to obtain a first configuration, wherein the first and the second capacitor are connected in parallel, operating the switching means to obtain a second configuration, wherein the first and the second capacitor are connected in series, storing energy in the capacitors using energy received from a wireless inductive power transmission, powering the data processing means on the data carrier, using the stored energy, and switching between the two configurations in time controlled by a data stream to be transmitted from the data carrier.

This provides a method of operating a monitoring device with a reduced power consumption.

Further advantageous features appear from the dependent claims.

Still other features of the present invention will become apparent to those skilled in the art from the following description wherein embodiments of the invention will be explained in greater detail.

BRIEF DESCRIPTION OF THE DRAWINGS

By way of example, there is shown and described a preferred embodiment of this invention. As will be realized, the invention is capable of other embodiments, and its several details are capable of modification in various, obvious aspects all without departing from the invention. Accordingly, the drawings and descriptions will be regarded as illustrative in nature and not as restrictive. In the drawings.

DETAILED DESCRIPTION OF THE INVENTION

Figure 1:
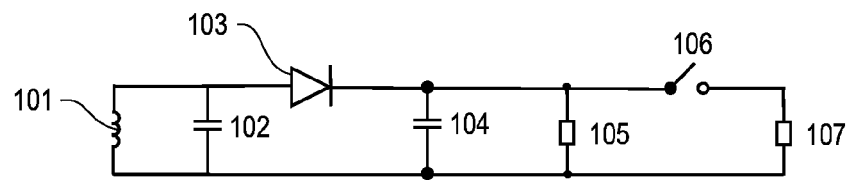
FIG. 1 illustrates an equivalent circuit diagram of a prior art data carrier in a first state of operation.

Reference is first made to FIG. 1, which illustrates an equivalent circuit diagram of a prior art data carrier. The data carrier is shown in a first state of operation wherein the data carrier is set primarily for receiving power wirelessly supplied from a reader. The circuit diagram comprises a receiver coil 101 and a resonance capacitor 102 that together form a resonant circuit that is tuned to a resonance frequency that corresponds to the transmission frequency of the wireless signal from the reader. The circuit diagram further comprises a rectifier 103, an energy storage capacitor 104, a resistor 105 representing the load of the monitoring and data processing means on the data carrier, a switch 106, and a modulation resistor 107.

A small part of the wireless signal from the reader couples to the receiver coil 101, and induces a voltage across the receiver coil. The voltage is rectified in rectifier 103, and as a result energy is stored in the energy storage capacitor 104.

Figure 2:
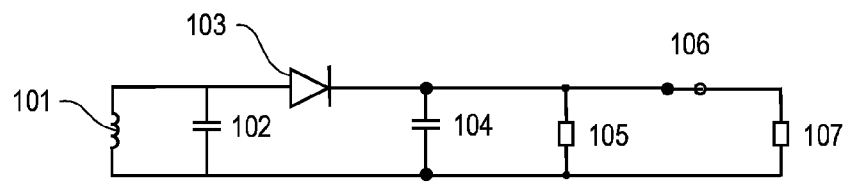
FIG. 2 illustrates an equivalent circuit diagram of the prior art data carrier of FIG. 1 in a second state of operation.

Reference is now made to FIG. 2, which illustrates an equivalent circuit diagram of the prior art data carrier of FIG. 1 in a second state of operation. In the first state of operation the switch 106 is open and in the second state the switch 106 is closed. When the switch 106 is closed the modulation resistor 107 is coupled in parallel with the load resistor 105.

A switching on and off of the modulation resistor 107 brings about a change in impedance of the transmitter coil in the reader (to be described below) when the reader and data carrier are inductively coupled. This has the effect of an amplitude modulation of a voltage in the reader. Therefore data can be transmitted from data carrier to reader if the timing of the switching of the modulation resistor 107 is controlled by the data to be transmitted from the data carrier and to the reader. This type of load modulation is disadvantageous in that the voltage across the load resistor 105 may vary during the load modulation and in that power is dissipated as heat in the modulation resistor 107.

Further details concerning prior art data carriers adapted for wireless power supply and wireless data transmission using load modulation of the data carrier can be found in the book by Klaus Finkenzeller: "RFID handbook: fundamentals and applications in contactless smart cards and identification", John Wiley & Sons, (2003).

Figure 3:
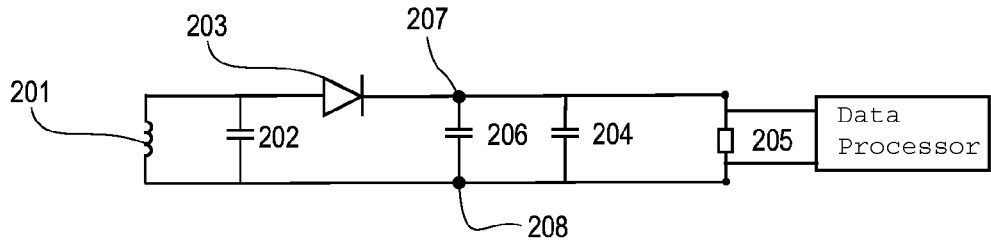
FIG. 3 illustrates an equivalent circuit diagram of a data carrier, according to a first embodiment of the invention, in a first state of operation.

Reference is now made to FIG. 3 which illustrates an equivalent circuit diagram of a data carrier, according to a first embodiment of the invention. The rest of the monitoring device (i.e. the reader) is omitted from the drawing in order to improve clarity. The data carrier is shown in a first state of operation wherein the data carrier is set primarily for receiving power wirelessly supplied from a reader. The circuit diagram comprises a receiver coil 201, a resonance capacitor 202, a rectifier 203, an energy storage capacitor 204, a resistor 205 representing the load of the monitoring and data processing means on the data carrier, a modulation capacitor 206 and connection points 207 and 208.

Figure 4:
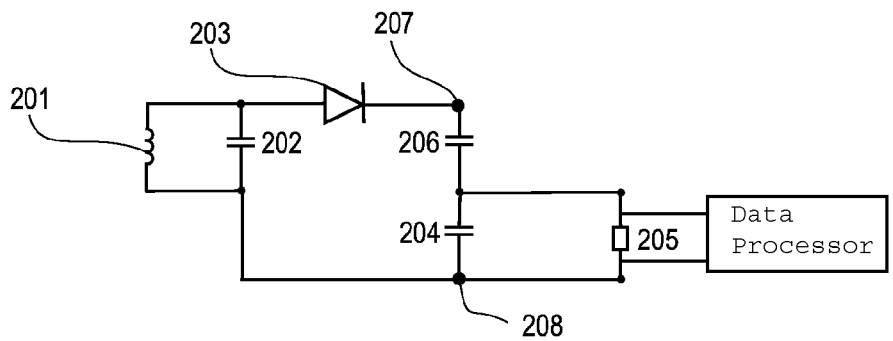
FIG. 4 illustrates an equivalent circuit diagram of the data carrier, according to the first embodiment of the invention, in a second state of operation.

Reference is now made to FIG. 4 which illustrates an equivalent circuit diagram of the data carrier of FIG. 3, according to the first embodiment of the invention. The rest of the monitoring device (i.e. the reader) is again omitted from the drawing in order to improve clarity. The data carrier is shown in a second state of operation where the load of the data carrier, as seen from the reader, is changed relative to the first state of operation. The circuit diagram again comprises the receiver coil 201, the resonance capacitor 202, the rectifier 203, the energy storage capacitor 204, the resistor 205 representing the load of the monitoring and data processing means on the data carrier, the modulation capacitor 206 and the connection points 207 and 208.

In the first state of operation the data carrier according to the first embodiment of the invention forms a low impedance resonant circuit, as seen from a reader inductively linked to the data carrier. In the second state of operation the data carrier forms a high impedance resonant circuit. By switching between the two operating states in time with a data stream to be transmitted from the data carrier and to the reader it becomes possible to reconstruct the data stream in the reader based on an appropriate evaluation procedure in the reader.

It is a specific advantage of the present invention that load modulation is achieved with only negligible power dissipation in the components used for the load modulation.

According to an embodiment the capacitance of the energy storage capacitor 204 is between 2 and 10 times larger than the capacitance of the modulation capacitor 206 and the capacitance of the energy storage capacitor 204 is in the range between 5 and 20 nF, while the capacitance of the modulation capacitor 206 is in the range between 0.5 and 10 nF. Preferably the capacitance of the energy storage capacitor is 10 nF and the capacitance of the modulation capacitor is 1 nF.

According to another embodiment the ratio of the capacitances of the modulation capacitor 206 and the energy storage capacitor 204 is in the range between 0.5 and 2. Preferably the capacitances of the two capacitors are nominally identical and in the range between 0.5 nF and 20 nF.

Figure 5:
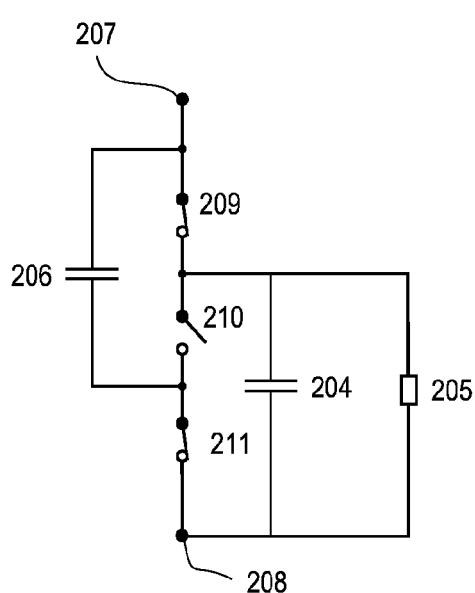
FIG. 5 illustrates, in higher detail, the modulation portion of the data carrier, according to the first embodiment of the invention, in the first state of operation.

Reference is now made to FIG. 5 which illustrates the modulation portion of the data carrier, in higher detail, according to the first embodiment of the invention. FIG. 5 illustrates the energy storage capacitor 204, the modulation capacitor 206, switches 209, 210 and 211 and connection points 207 and 208. FIG. 5 illustrates the data carrier, when it is in the first state of operation. In this first state of operation the switches 209 and 211 are closed, and the switch 210 is open. The capacitors 204 and 206 are thus connected in parallel relative to the connection points 207 and 208.

Figure 6:
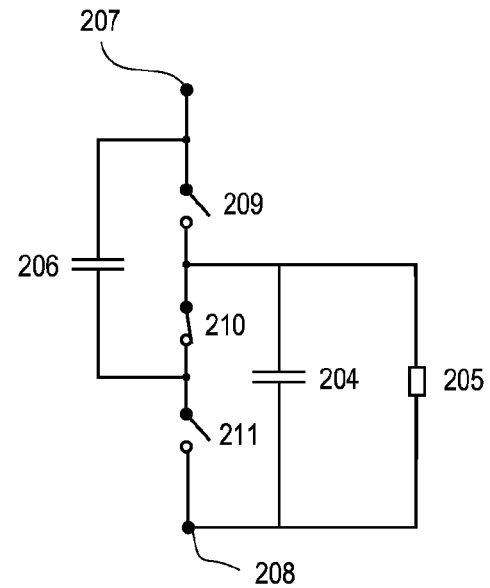
FIG. 6 illustrates, in higher detail, the modulation portion of the data carrier, according to the first embodiment of the invention, in the second state of operation.

Reference is now made to FIG. 6 which illustrates the modulation portion of the data carrier, in higher detail, according to the first embodiment of the invention. FIG. 6 illustrates the energy storage capacitor 204, the modulation capacitor 206, switches 209, 210 and 211 and connection points 207 and 208. FIG. 6 illustrates the data carrier, when it is in the second state of operation. In this second state of operation the switches 209 and 211 are open, and the switch 210 is closed. The capacitors 204 and 206 are thus connected in series relative to the connection points 207 and 208.

According to the first embodiment of the invention the resistor 205 is coupled in parallel to the energy storage capacitor 204 in both the first and second state of operation. In this way the voltage across the resistor 205 is kept relatively constant independent on the state of operation. The resistor 205 of the equivalent circuit represents the monitoring and data processing means of the data carrier and the corresponding voltage regulation means. A too high voltage drop across the voltage regulation means will result in unnecessary power dissipation.

It is an advantage of the present invention that energy is supplied to the energy storage capacitor 204 and the modulation capacitor 206 during both the first and the second state of operation. If the high impedance resonant circuit, as seen from the reader, formed in the second state of operation was simply an open circuit the power transmitted from the reader during this state of operation would not be used to supply energy to the data carrier.

Therefore the power efficiency of a monitoring device including a reader and a data carrier, according to the invention, can be very high.

Figure 7:
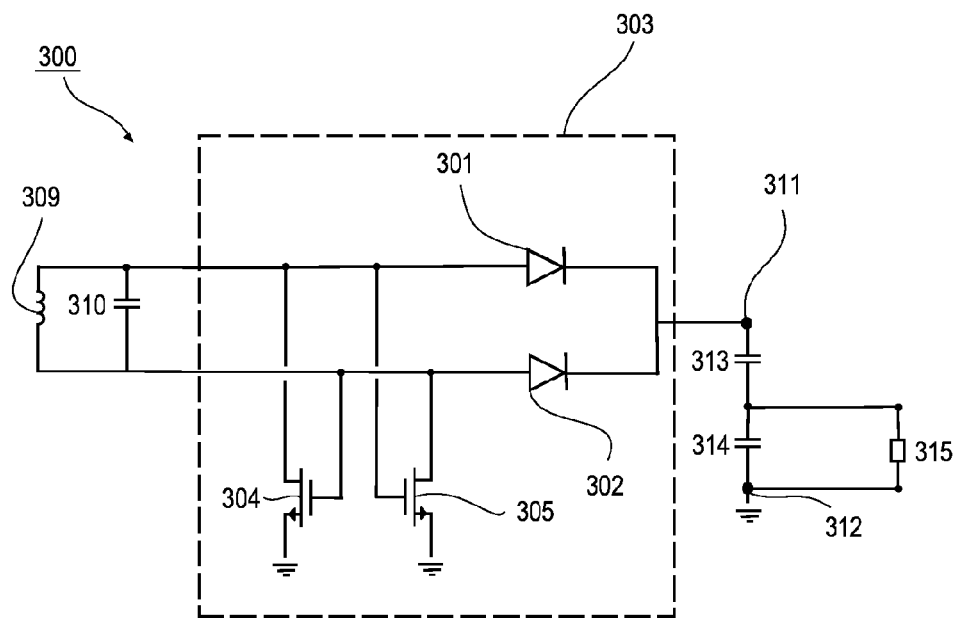
FIG. 7 illustrates an equivalent circuit diagram of the data carrier, according to a second embodiment of the invention, in a second state of operation.

Reference is now made to FIG. 7, which illustrates an equivalent circuit diagram of a data carrier 300, according to a second embodiment of the invention. The rest of the monitoring device (i.e. the reader) is again omitted from the drawing in order to improve clarity. The data carrier is shown in a second state of operation wherein the data carrier is set primarily for receiving power wirelessly supplied from a reader. The circuit diagram comprises receiver coil 309, resonance capacitor 310, rectifier 303, energy storage capacitor 314, resistor 315 representing the load of the monitoring and data processing means on the data carrier, modulation capacitor 313 and connection points 311 and 312. The rectifier 303 includes two diodes 301 and 302 and two switching transistors 304 and 305. When the voltage induced in the receiver coil 309 is in its positive half-wave period the diode 301 is forward biased and current flows towards the connection point 311. During this period the switching transistor 304 is in its "OFF" state and the switching transistor 305 is in its "ON" state, hereby the current flow is allowed to return to the receiver coil through the switching transistor 305. When the voltage induced in the receiver coil 309 is in its negative half-wave period the diode 302 is forward biased and current flows again towards the connection point 311. During this period the switching transistor 304 is in its "ON" state and the switching transistor 305 is in its "OFF" state, whereby the current flow is allowed to return to the receiver coil through the switching transistor 304.

Hereby full-wave rectification is achieved with a circuit having only two diodes, and in each one of the half-wave periods only a single diode is active. Hereby the total voltage drop of the rectifier circuit can be about a single diode voltage drop. This is a significant improvement compared to traditional rectifier bridges where the total voltage drop is about two times the single diode voltage drop.

In addition the rectifier circuit according to the second embodiment of the invention only consists of components that are small compared to e.g. rectifier circuits based on resistors and switching transistors.

Figure 8:
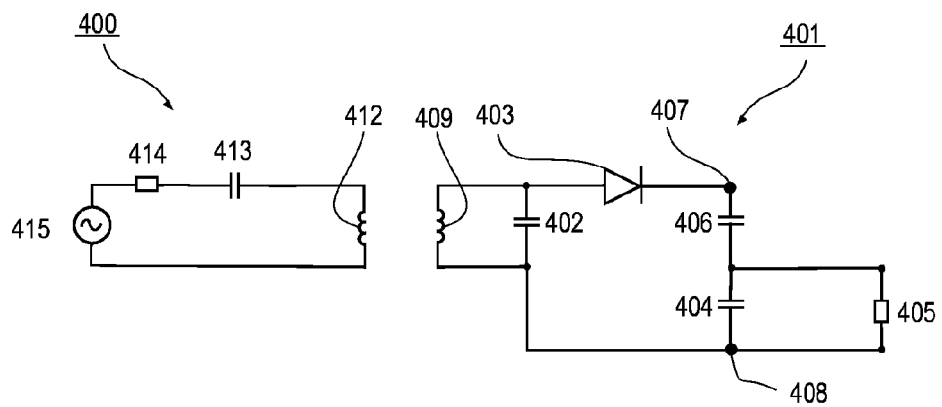
FIG. 8 illustrates an equivalent diagram of a monitoring device incorporating a reader and a data carrier according to a third embodiment of the invention.

Reference is now made to FIG. 8, which illustrates an equivalent circuit diagram for a monitoring device according to a third embodiment of the invention. The monitoring device has a reader 400 and a data carrier 401. The reader 400 includes a signal generator 415, a resonance resistor 414, a resonance capacitor 413 and a transmitter coil 412. The resonance resistor 414, resonance capacitor 413 and transmitter coil 412 together form a resonant circuit that is tuned to a resonance frequency that corresponds to the chosen transmission frequency of the wireless signal from the reader part. The data carrier 401 includes a receiver coil 409, a resonance capacitor 402, a rectifier 403, an energy storage capacitor 404, a resistor 405 representing the load of the monitoring and data processing means on the data carrier, a modulation capacitor 406 and connection points 407 and 408. The data carrier 401 is similar to the data carriers described with reference to FIG. 3 and FIG. 4.

The signal generator 415 generates an alternating current in the transmitter coil 412. The current in the transmitter coil generates an alternating magnetic field which induces an alternating current in the receiver coil 409. The frequency of the alternating magnetic field is denoted the operating frequency. The current in the receiver is used to power the data carrier.

According to an embodiment the data carrier is implanted in a human being for continuous surveillance of a specific medical condition in the user. According to a further embodiment the data carrier has electrode means for recording EEG signals of a user and the data carrier is subcutaneously implanted in the user.

According to another embodiment the operating frequency is in the range between 900 kHz and 1100 kHz, preferably about 1 MHz. Hereby is provided a monitoring device which can be made smaller than devices having a lower operating frequency because the requirements to the minimum size of the coils are relaxed when the operating frequency is increased. For a given design of the coil and with a given load of the data carrier, the Q factor of the resonance circuit on the data carrier will generally increase with the operating frequency. For a monitoring device according to various embodiments of the invention this proportionality starts to diminish about 1 MHz due to the skin effect.

It has been found that the resonance capacitor 202, 310 and 402 at an operating frequency of 1 MHz can have a capacitance in the range between 25 pF and 75 pF, preferably about 50 pF, which is well above the parasitic capacitances. As opposed to this, a resonance capacitor with a capacitance in the range between 2 and 5 pF is required for an operating frequency of 10 MHz. Such small capacitance values are difficult to implement because they are too similar to the parasitic capacitances.

On the other hand it has been found that the power efficiency of the monitoring device can be increased with a factor of say 4 by increasing the operating frequency from 100 kHz to 1 MHz.

Other modifications and variations of the structures and procedures will be evident to those skilled in the art.

We claim:

1. A monitoring device comprising a reader and a data carrier, adapted for wireless data transmission from the data carrier to the reader using load modulation whereby a load presented by said data carrier is modulated, and for powering the data carrier using a wireless inductive power transmission via an inductive link from the reader and to the data carrier, wherein the data carrier comprises:
   a receiver coil;
   a data processor for processing data stored on said data carrier;
   a rectifier for rectifying an output of the receiver coil;
   a switch; and
   a capacitor circuit of at least two capacitors connected to said rectifier;

wherein the data processor, switch and capacitors are connected such that, in a first configuration, the capacitors are coupled in parallel and, in a second configuration, the capacitors are coupled in series, whereby load modulation of the data carrier is achieved by switching between said first and second configuration, and said capacitors are further arranged for storing energy received from the wireless inductive power transmission and for powering the data processor.

2. The monitoring device according to claim 1, wherein in the second configuration, the capacitors are coupled in series and the data processor is coupled in parallel with one of the capacitors.

3. The monitoring device according to claim 1, wherein the ratio of the capacitance of a first capacitor relative to the capacitance of a second capacitor is in the range between 0.5 and 2.

4. The monitoring device according to claim 1, wherein the rectifier comprises a first and a second diode and a first and second switching transistor configured such that a first end of the receiver coil is connected to the collector of the first switching transistor, the base of the second switching transistor and the input of the first diode, and the second end of the receiver coil is connected to the collector of the second switching transistor, the base of the first switching transistor and the input of the second diode.

5. The monitoring device according to claim 4, adapted for implementing an operating frequency of the inductive link between the reader and data carrier in the range between 900 kHz and 1100 kHz.

6. A method of operating a data carrier in a monitoring device comprising the steps of
providing in the data carrier a capacitor circuit including a first capacitor, a second capacitor and a switch, as well as a data processor,
connecting the capacitor circuit and the data processor, and operating the switch to obtain a first configuration, wherein the first and the second capacitor are connected in parallel,
operating the switch to obtain a second configuration, wherein the first and the second capacitor are connected in series,
storing energy in the capacitors using energy received from a wireless inductive power transmission,
powering the data processor on the data carrier, using the stored energy, and
switching between the two configurations in time controlled by a data stream to be transmitted from the data carrier.

* * * * *